(12) United States Patent
Howe et al.

(10) Patent No.: US 8,895,931 B2
(45) Date of Patent: Nov. 25, 2014

(54) MONITORING INSTRUMENT

(75) Inventors: Geoffrey Stuart Howe, Newton Aycliffe (GB); David Charles Banks, Hartlepool (GB)

(73) Assignee: Johnson Matthey PLC, London (GB)

( * ) Notice: Subject to any disclaimer, the term of this patent is extended or adjusted under 35 U.S.C. 154(b) by 0 days.

(21) Appl. No.: 13/806,588

(22) PCT Filed: Jun. 24, 2011

(86) PCT No.: PCT/GB2011/051197
§ 371 (c)(1), (2), (4) Date: Mar. 18, 2013

(87) PCT Pub. No.: WO2011/161468
PCT Pub. Date: Dec. 29, 2011

(65) Prior Publication Data
US 2013/0168554 A1    Jul. 4, 2013

(30) Foreign Application Priority Data

Jun. 24, 2010  (GB) .................................. 1010640.9

(51) Int. Cl.
*G01N 23/00* (2006.01)
*G01D 11/24* (2006.01)
*G01D 11/26* (2006.01)

(52) U.S. Cl.
CPC .............. *G01N 23/00* (2013.01); *G01D 11/245* (2013.01); *G01D 11/26* (2013.01)
USPC ..................................................... 250/358.1

(58) Field of Classification Search
CPC ....... G01M 3/005; G01M 3/18; G01M 3/243; G01N 2021/1793; G01N 25/72; G01N 23/223; G01N 23/00

USPC ....................................................... 250/358.1
See application file for complete search history.

(56) References Cited

U.S. PATENT DOCUMENTS 3,889,522 A  *  6/1975  Mayo ......................... 73/40.5 R
4,335,308 A  *  6/1982  Caldecourt et al. ........ 250/358.1
(Continued)

FOREIGN PATENT DOCUMENTS

DE          1 165 159 B      3/1964
GB          2457888 A   *    9/2009
(Continued)

OTHER PUBLICATIONS

International Search Report dated Dec. 15, 2011, from PCT International Application No. PCT/GB2011/051197.
British Search Report dated Sep. 29, 2010, from British Patent Application No. 1010640.9.

*Primary Examiner* — Marcus Taningco
(74) *Attorney, Agent, or Firm* — RatnerPrestia

(57) ABSTRACT

The invention comprises an apparatus comprising a waterproof housing assembly comprising a housing (20) and a display panel (10, 32), and incorporating an enclosure (30) containing electrical apparatus, wherein said display panel is formed from a clear material (16) encapsulating a visual display (12) and/or a light-source (34) and said apparatus is capable of operating in water at a pressure of at least 300 bar without ingress of water into the enclosure. The apparatus may be used as an instrument or a lighting unit in sub-sea environments. The invention comprises further a light-source attachment for a powered apparatus comprising a light source embedded within a block of clear material (16) and means for mounting said block on the powered apparatus such that a connector connects the light source to a power source within the powered apparatus.

24 Claims, 2 Drawing Sheets

(56) References Cited

U.S. PATENT DOCUMENTS

| | | |
|---|---|---|
| 5,184,064 A | 2/1993 | Vicknair et al. |
| 2003/0020456 A1 | 1/2003 | Ayo et al. |
| 2005/0255325 A1 | 11/2005 | Inagaki |
| 2006/0187652 A1 | 8/2006 | Doyle |
| 2007/0268153 A1 | 11/2007 | Gansen |
| 2011/0098947 A1* | 4/2011 | Fattah .................. 702/53 |

FOREIGN PATENT DOCUMENTS

| | | |
|---|---|---|
| JP | 63-238514 A | 10/1988 |
| JP | 8-159820 A | 6/1996 |
| JP | 11-44557 A | 2/1999 |

* cited by examiner

MONITORING INSTRUMENT

CROSS-REFERENCE TO RELATED APPLICATIONS

This application is the U.S. National Phase application of PCT International Application No. PCT/GB2011/051197, filed Jun. 24, 2011, and claims priority of British Patent Application No. 1010640.9, filed Jun. 24, 2010, the disclosures of both of which are incorporated herein by reference in their entireties for all purposes.

FIELD OF THE INVENTION

The present invention concerns a display suitable for use with instruments and lighting apparatus which are subjected to high pressure and changes of pressure.

BACKGROUND OF THE INVENTION

The oil and gas exploration industry makes use of a variety of instruments for measuring and controlling certain operations at depths of several thousand meters under the sea. For example an instrument which has been used for tracking pipeline pigs includes a radiation monitor and a data processor for detecting and recording the passage of a pig in its vicinity. The instrument display, showing the number of pigs detected and other information, can be read by a diver or remotely operated vehicle (ROV) deployed for the purpose. This known instrument is housed in a rugged and pressure-resistant metal housing, with the display visible through a glass lens. The lens is itself relatively thick and resistant to pressure down to about 3000 m. A problem encountered with these instruments is that the lenses are susceptible to breakage, particularly during an operation to retrieve the instrument from deep locations. The lens is therefore replaced between each deployment, thus increasing the cost of the instrument over its lifetime. A similar problem occurs with lights which are used in sub-sea conditions, e.g. portable lighting units used by divers or an ROV. It is an object of the invention to provide a display that overcomes this problem.

SUMMARY OF THE INVENTION

According to the invention, we provide a display panel for an instrument comprising a visual display of at least one status or measurement which is monitored by the instrument, characterised in that said visual display is coated over an entire visually outwardly facing surface with a layer of a clear material.

By visually outwardly facing surface of the display, we mean the surface of the display on which the indicators of status or measurement are read, i.e. the surface that a user would look at to read the display.

The display panel is suitable for use in the pig-tracking instrument described above because it avoids the use of the glass lens and therefore enables the instrument to be deployed at depth and recovered many times without requiring repair to the display. The visual display panel of the invention is not, however, limited to use in such an instrument.

According to a second aspect of the invention, we provide an instrument comprising a radiation detector, a power source for said radiation detector and a data processor/controller, all being housed within a pressure-resistant, water-proof housing and further comprising a visual display panel comprising a visual display of at least one status or measurement which is monitored by the instrument, characterised in that said visual display is coated over an entire visually outwardly facing surface with a layer of a clear material.

Preferably the visual display is substantially embedded in the clear material. In this case, the display panel comprises the visual display embedded within a block of the clear material and has means for connecting the embedded display to electrical equipment, e.g. a data processor/controller and/or power source, within, or external to, the housing. The instrument is preferably a monitoring instrument.

According to a third aspect of the invention, we provide a lighting unit comprising a power-source and a light-source, said power-source being housed within a pressure-resistant, water-proof housing assembly, said housing assembly comprising a housing and a display panel, characterised in that said display panel comprises a clear material in which said light-source is embedded. Preferably the housing assembly incorporates an enclosure which may contain said power source. Optionally the power source is located outside the housing assembly enclosure, for example within an ROV or a powered installation.

According to a fourth embodiment, we provide an apparatus comprising a water-proof housing assembly comprising a housing and a display panel, and incorporating an enclosure containing electrical apparatus, said display panel being formed from a clear material encapsulating a visual display and/or a light-source and characterised in that said apparatus is capable of operating in water at a pressure of at least 300 bar without ingress of water into the enclosure.

According to a fifth embodiment of the invention, we provide an apparatus comprising an electrically operated light source which is wholly or partially covered on all of its major surfaces with a layer of a clear material and incorporating means to connect said light source to a source of power.

BRIEF DESCRIPTION OF THE DRAWINGS

The invention will be further explained with reference to the accompanying drawings, shown for example only. The drawings are schematic representations of.

DETAILED DESCRIPTION OF THE INVENTION

Figure 1:
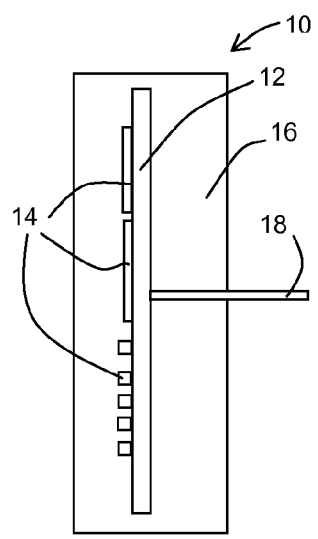
FIG. 1: a cross-section through a display according to the invention.

The term "encapsulating" is intended to mean that the display or light-source is totally enclosed within a layer of the clear material, with the exception of a portion forming an electrical connection which can be connected to a power source, control or processing means or other electrical apparatus. The term "embedded" is intended to mean that the embedded object, i.e. the light-source or display, is totally surrounded by a layer of the clear material, with the exception of a portion forming an electrical connection as described above. Normally the major surfaces of the embedded object are coated by the clear material in which it is embedded.

In a preferred embodiment, the enclosure contains electrical apparatus comprising a power supply and powered electrical equipment which is connected to the display or light source encapsulated in the material forming the display panel. The electrical apparatus may comprise an electrically-powered measurement and control means. Alternatively, the electrical equipment may comprise means for connecting the power supply to a light source and optionally means for controlling the operation of a light source or display which is encapsulated within the material forming the display panel.

The visual display may include one or more indicator lights, an alphanumeric display, a counter, a screen, pixel-addressable display or other means of indicating, visually, a status or measurement monitored by the instrument. The visual display panel may incorporate a light source for illuminating the display itself or for illuminating an area outside the housing.

The display panel is formed from a clear material which is capable of encapsulating a display or light source. The material is preferably a clear resin. The display or light source is preferably embedded within a block of the resin. The display panel material is sufficiently tough, in use, to be resistant to deformation when subjected to an operating pressure against the face of the display of at least 300 bar (30 MPa), more preferably at least 500 bar (50 MPa) at a temperature of less than 20° C., more preferably less than 10° C., especially at temperatures experienced in deep sub-sea locations, approximately 4° C. The resistance of the material to deformation is preferably such that a display panel comprising the clear material and the visual display panel or light exhibits a deformation at its edge of less than 0.1 mm when subjected to a pressure against its outwardly-facing surface of at least 300 bar, more preferably at least 500 bar. The material preferably has a modulus of elasticity in compression of at least 3 GPa and a compressive strength of at least 30 MPa. The block of clear material incorporating the display or light-source is preferably at least 10 mm thick and more preferably at least 25 mm thick. The clear material forming the display panel may include means for forming a waterproof connection with other parts of the instrument, e.g. in the form of a channel for location of a seal such as a gasket.

The clear material has thermal properties which are suitable for the application for which the display is intended. For example, an instrument which is to be used for sub-sea oil and gas exploration must be capable of withstanding ambient temperatures at the surface as well as those at depth. The display usually incorporates electronic components. The clear material is therefore preferably substantially non-conducting, i.e. of high resistance. Preferably the material has a volume resistivity of at least 10 G ohm m. The material is clear, meaning that it transmits visual light without significant distortion, such that the display is sufficiently visible to be read and interpreted accurately through the thickness of the resin covering the display. The material is preferably sufficiently resistant to impact for the display to be used in an industrial application, including sub-sea deployment and use. If necessary, additional protective components may be provided to protect the display from impact, such as a protective mesh or a reinforcing member. Generally, however, the use of the display of the invention provides a rugged display which is more robust and resistant to general handling and transport than a display incorporating a glass lens and may not require additional protective measures. The clear material is preferably a clear polymer or resin. Suitable resins include polyurethanes, polyesters, epoxy resins, acrylic resins. These and other resins which are known and used as electrical potting resins, are suitable for the present invention, provided their physical and thermal properties meet the requirements of the application, in particular the requirements discussed above.

The material covering the display may be flat or shaped, for example convex, concave or otherwise contoured. For example the surface of the resin coating may be shaped to enhance or magnify the appearance or readability of the visual display. The material may be shaped so as to form a lens, for example to improve the focus of the display or to focus light from a light-source to form a beam or point of illumination.

A resin block in which a display or light-source is wholly or partially embedded may be made by forming the resin block around the display or light-source, for example by casting a flowable composition which can be cured to form the resin in a mould. The mould may contain the display or light-source before the resin is formed by curing. Alternatively, the clear resin may be formed into parts which can be joined around the display or light-source, for example by means of an adhesive.

The display or light-source is also preferably coated on a surface other than the visually outwardly facing surface with a layer of clear material. The display or light-source is preferably coated with a layer of clear material, wholly or partly on all of its major surfaces. The display or component on which the display is made is preferably substantially embedded in the material forming the display panel. All of its surfaces are preferably wholly or partially covered in the clear material. The display or light source is preferably substantially surrounded by the clear material. The display panel may therefore be wholly or partially embedded in a layer or block of clear material, which is preferably a resin, especially a clear resin. In such a case, means for connecting the display to the data processor/controller and power source must be provided. Preferably the encapsulating material, such a resin block, is formed with a channel or opening through which an electric cable or other electrical connection means may extend to/from the display or light-source. The block or layer of resin may have a means for engaging and disengaging a powered apparatus, such as a remotely operated vehicle or a portable light, the engagement means preferably incorporating a connection for providing power and/or control signals to the display or light source. The engagement means may comprise a standard connector which is adapted for connection to apparatus used in sub-sea operations in accordance with known standards in the industry. The display may also communicate with a data processor/controller, whether inside or external to the housing, by wireless means. For example, means may be provided for communicating with a data processor/controller monitor or detector, located within the housing, e.g. to receive and display a signal encoding data or a control instruction. The wireless means may be encapsulated in the clear material forming the display panel. When the block of clear material forming the unit contains a light-source, it may be engaged with a connector of an ROV in order to provide a replaceable light source to the ROV.

Accordingly we also provide, according to the invention, a display panel in the form of a light-source attachment for a powered apparatus comprising a light-source and a connector for connecting said light source to a source of power within the powered apparatus, characterised in that the light source is embedded within a block of a clear material, said block having said connector disposed on a surface thereof, and means for mounting said block on said powered apparatus in such a way that the connector connects said light source to said source of power. The powered apparatus may comprise a remotely operated vehicle having a connector with which the connector mounted on the block is adapted to form a mechanical and/or electrical engagement.

The housing and display panel are assembled to form a housing assembly incorporating an enclosure and which is resistant to the ingress of water into the enclosure under pressure. The display panel is supported by the housing in order to minimise deformation. At least one O-ring or gasket made of resilient material such as a nitrile rubber is provided between the housing and the display panel in order to seal the enclosure against the ingress of water. The number and placement of gaskets or O-rings may be determined by the skilled person to be suitable for the prevention of water-ingress into an enclosure formed from the housing and the display panel material. As an example, a circular display panel having a diameter of about 150 mm and a thickness of about 25 mm which is cast from a clear epoxy resin and incorporates an electrically-operated numerical display is assembled to an end-plate of a cylindrical housing with two concentric O-rings (100 mm and 50 mm) placed between the end plate and the display panel.

In order to test the assembly for water resistance under pressure, the assembly is placed into a pressure test vessel which is filled with water to a level at which the housing assembly is covered by up to 100 mm of water. A pump is used to increase the vessel pressure to at least 300 bar (30 MPa), preferably at least 400 bar (40 MPa), and optionally to at least 500 bar (50 MPa), over a period of 1 minute. The pressure is then released over a period of 1 minute, until the vessel pressure is equalised with atmospheric pressure. This is one pressurisation and depressurisation cycle. The pressurisation and depressurisation cycle is repeated at least 100 times, preferably at least 200 times. The repeated pressurisation and depressurisation is intended to simulate normal operating conditions of a sub-sea apparatus, in which the housing and display panel assembly forming the enclosure is repeatedly dived to a depth at which the enclosure will be subjected to high water pressure. After the test has been completed, the housing/display panel assembly is inspected visually to determine whether water has penetrated into the enclosure. The housing assembly of the invention does not allow water to enter the enclosure during 100 cycles, and preferably during 200 cycles, of pressurisation to 300 bar and depressurisation. More preferably, the housing assembly of the invention does not allow water to enter the enclosure during 100 cycles of pressurisation to 500 bar and depressurisation.

A second test may also be performed in which the pressure in the test vessel is maintained at a high pressure, e.g. 300-400 bar for a period of 2 weeks. This simulates a long term deployment of the subsea housing. After the test has been completed, the housing/display panel assembly is inspected visually to determine whether water has penetrated into the enclosure. The housing and display panel assembly of the invention does not allow water to enter the enclosure during pressurisation to at least 300 bar for 2 weeks. More preferably, the housing and display panel assembly of the invention does not allow water to enter the enclosure during pressurisation to at least 500 bar for 2 weeks.

The apparatus may be or be a part of a lighting unit, a measuring instrument or control apparatus. The display is particularly suitable for use as part of a monitoring instrument according to the invention. Such a monitoring instrument may comprise a radiation detector, a power source for said radiation detector and a data processor/controller, all being housed within a pressure-resistant, water-proof housing and further comprising a display panel having a visual display of at least one status or measurement which is monitored by the instrument, characterised in that said visual display is a display according to the invention, i.e. in which the visual display is encapsulated within a clear material forming the display panel. In such a monitoring instrument, the radiation detector may be any suitable detector. When the monitoring instrument is for monitoring ionising radiation such as gamma, beta or X-radiation the detector may be any suitable detector such as a scintillation detector, Geiger Müller tube, or semiconductor detector. The skilled person designing such an instrument can select the most appropriate form of detector for the particular monitoring application. The housing may contain wireless transmission and reception means for communicating with the encapsulated display.

The apparatus in the form of a radiation monitor is particularly suitable for monitoring the proximity of a pipeline pig which includes a source of radiation to enable the pig to be tracked. In this embodiment, the radiation detector housed within the housing is capable of detecting radiation emitted by the source of radiation mounted on a pipeline pig, and the data processor determines the proximity of a pipeline pig from the radiation detected by the detector. The visual display includes a counter for displaying a number of pipeline pigs determined by the data processor, and optionally other indications such as battery life or the amount of radiation detected by the detector.

The apparatus may comprise a measuring and/or control apparatus for measuring and controlling an instrument remotely. In such a case the apparatus may comprise wireless means for communicating with a data processor/controller monitor or detector, located external to the housing, e.g. to receive and display a signal encoding data or a control instruction from a remote instrument. The wireless means may be encapsulated with in the clear material forming the display panel or may be located within the housing.

When the apparatus is a lighting unit, the light-source preferably comprises a low-power light-source such as one or more light-emitting diodes.

The housing is made from material which is sufficiently robust to withstand the conditions in which the apparatus is required to operate. For sub-sea deployment the housing is typically made from a metal such as steel, although other materials such as strong polymeric materials, optionally reinforced with metal components, may be used. The material is of sufficient thickness to withstand the operating conditions of the apparatus, especially high pressure environments such as those encountered under water. The housing is preferably formed in such a way as to be resistant to damage or deformation caused by external pressure. The housing may incorporate a handle and/or means for attachment to or engagement with an ROV so that the apparatus may be manoeuvred during use underwater. The clear material encapsulating the display or light may extend to cover one or more external surfaces of the housing.

FIG. 1 shows a display (10) according to the invention in which the visual display board (12), incorporating display items (14) such as lights, alphanumeric counters and a graphical display mounted on the surface of the display board. The display items are mounted by means of conventional electrical connectors and printed circuitry which are not shown. The electrical circuit components of the display board are connected to a ribbon cable (18). The display is encapsulated in a relatively thick (10-15 mm) layer of a clear epoxy resin (16) so that the resin covers all of the display board 12. The ribbon cable (18) extends through the resin so that power and electrical signals can pass to the display board.

Figure 2:
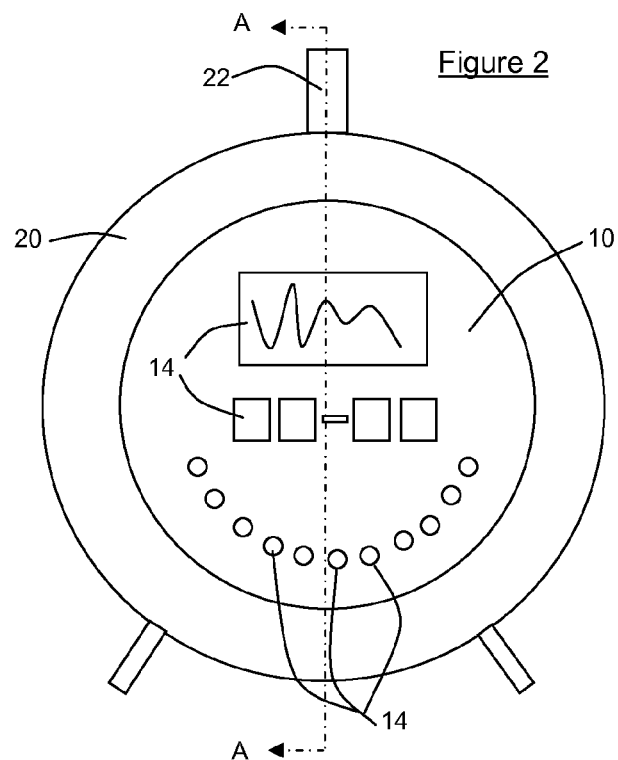
FIG. 2: a view from the front of an instrument according to the invention.
Figure 3:
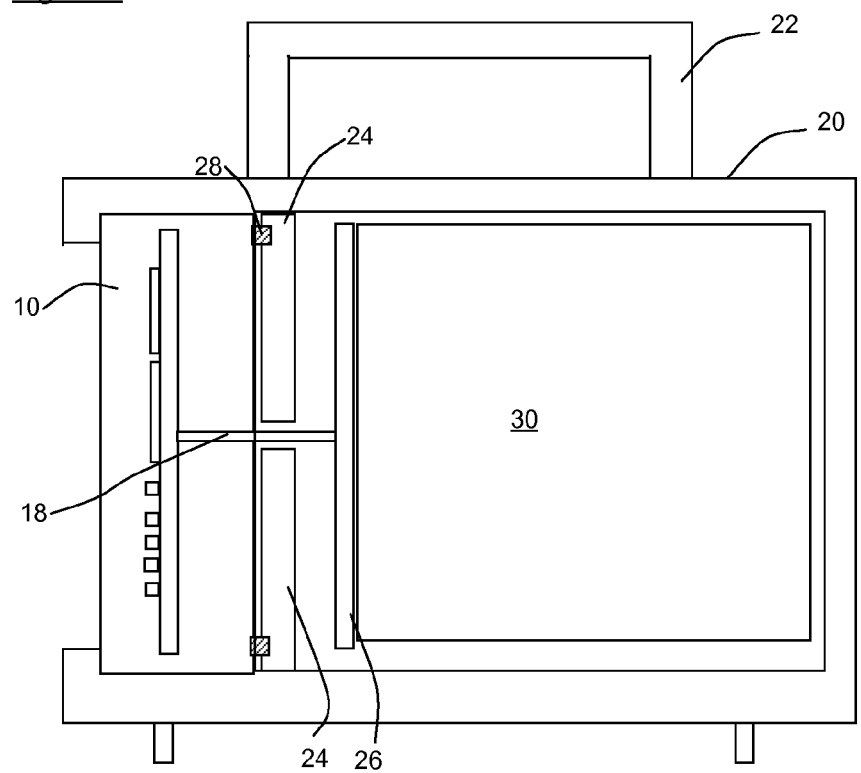
FIG. 3: a cross-section through the instrument shown in FIG. 2 along the lines A-A.

FIGS. 2 and 3 show an example of a monitoring instrument incorporating the display (10). The instrument comprises a pressure-resistant steel housing 20 having a handle (22). The display (10) is mounted at the front of the instrument adjacent a space in the housing in such a way that the visual display items can be viewed from the front. The display (10) is mounted against a plate (24) and sealed by means of an O-ring (28). The cable 18 passes through plate 24 to a display control board (26) which generates signals to control the visual display according to the function and status of the instrument. The housing also contains, within space 30, a power source and the detectors, etc. required for performing the monitoring function of the instrument. These have not been shown in detail. In the case of a particular embodiment of the instrument which is to be used for tracking pipeline pigs, the housing contains a radiation detector in the form of a scintillation detector, comprising a scintillation crystal and photomultiplier, together with a data processor and controller for controlling the operation of the instrument. A manual or remote operation interface (not shown) for switching the instrument on/off, changing its mode of operation, etc. is mounted on or within the housing, as appropriate.

Figure 4:
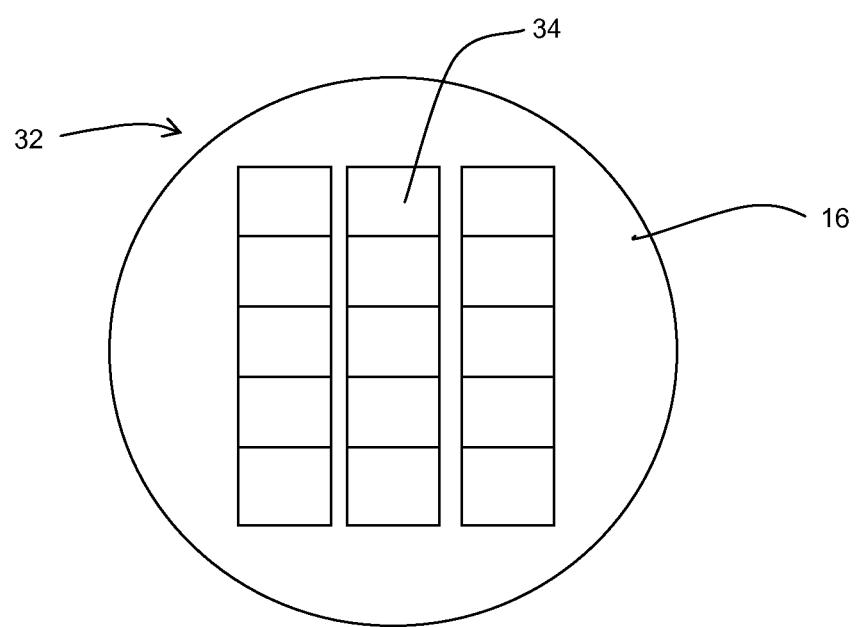
FIG. 4: a view of a display incorporating a light-source, according to the invention.

FIG. 4 shows a display (32) for a lighting unit. The display comprises three arrays of light-emitting diodes (LEDs) (34) embedded in a clear epoxy resin 16. This display is suitable for use as the display panel in a lighting unit. The display panel is assembled to a housing in a similar manner as that shown in FIG. 3, such that an electrical connection passing through the resin forming the display panel carries power and control signals between the LEDs and a power source and a control unit located within the housing.

The invention claimed is:

1. An apparatus in the form of a monitoring instrument for monitoring ionizing radiation comprising a water-proof housing assembly comprising a housing and a display panel, and incorporating an enclosure containing electrical apparatus, the electrical apparatus being housed within said enclosure and the electrical apparatus comprising a radiation detector for monitoring ionizing radiation, a power source for said radiation detector, and a data processor/controller, wherein said display panel is formed from a clear material encapsulating a visual display, said visual display displays at least one status or measurement related to ionizing radiation which is monitored by the monitoring instrument, wherein said apparatus is adapted for monitoring the proximity of a pipeline pig, said radiation detector is capable of detecting radiation emitted by a source of ionising radiation mounted on the pipeline pig, and said data processor determines the proximity of the pipeline pig from the radiation detected by the detector.

2. An apparatus according to claim 1, wherein the clear material has a modulus of elasticity in compression of at least 3 GPa.

3. An apparatus according to claim 1, wherein the clear material has a compressive strength of at least 30 MPa.

4. An apparatus according to claim 1, wherein the clear material has a volume resistivity of at least 10 G ohm m.

5. An apparatus according to claim 1 wherein the clear material comprises a resin selected from the group consisting of polyurethanes, polyesters, epoxy resins, polycarbonate and acrylic resins.

6. An apparatus according to claim 1, wherein the visual display is substantially embedded within the clear material.

7. An apparatus according to claim 1, wherein a channel or opening is provided through the encapsulating material through which an electrical connection may pass.

8. An apparatus according to claim 1, wherein said visual display includes a counter for displaying a number of pipeline pigs determined by the data processor.

9. An apparatus according to claim 1, further comprising wireless communication means by which the display may receive a signal from a transmitter within the housing.

10. An apparatus according to claim 1, further comprising wireless communication means by which the display may receive a signal from a transmitter external to the housing.

11. An apparatus according to claim 1, wherein said housing has a handle or means for engaging a remotely-operated vehicle.

12. An apparatus according to claim 1 further comprising a light source.

13. An apparatus according to claim 8, wherein the clear material has a modulus of elasticity in compression of at least 3 GPa.

14. An apparatus according to claim 8, wherein the clear material has a compressive strength of at least 30 MPa.

15. An apparatus according to claim 8, wherein the clear material has a volume resistivity of at least 10 G ohm m.

16. An apparatus according to claim 8, wherein the clear material comprises a resin selected from the group consisting of polyurethanes, polyesters, epoxy resins, polycarbonate and acrylic resins.

17. An apparatus according to claim 8, wherein the visual display is substantially embedded within the clear material.

18. An apparatus according to claim 8, wherein a channel or opening is provided through the encapsulating material through which an electrical connection may pass.

19. An apparatus according to claim 8, further comprising wireless communication means by which the display may receive a signal from a transmitter within the housing.

20. An apparatus according to claim 8, further comprising wireless communication means by which the display may receive a signal from a transmitter external to the housing.

21. An apparatus according to claim 8 further comprising a light source.

22. An apparatus according to claim 8, wherein the at least one status or measurement is related to radiation received from said source of radiation mounted on the pipeline pig.

23. An apparatus according to claim 1, wherein said apparatus is capable of operating in water at a pressure of at least 300 bar without ingress of water into the enclosure.

24. An apparatus according to claim 8, wherein said apparatus is capable of operating in water at a pressure of at least 300 bar without ingress of water into the enclosure.

* * * * *